US00PP27386P3

(12) United States Plant Patent
Bergman

(10) Patent No.: US PP27,386 P3
(45) Date of Patent: Nov. 15, 2016

(54) ***CHRYSANTHEMUM* PLANT NAMED 'CIDZ0063'**

(50) Latin Name: *Chrysanthemum×morifolium*
Varietal Denomination: CIDZ0063

(71) Applicant: SYNGENTA PARTICIPATIONS AG, Basel (CH)

(72) Inventor: Wendy R. Bergman, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/756,192

(22) Filed: Aug. 14, 2015

(65) Prior Publication Data

US 2016/0057913 P1 Feb. 25, 2016

Related U.S. Application Data

(60) Provisional application No. 62/039,706, filed on Aug. 20, 2014.

(51) Int. Cl.
*A01H 5/02* (2006.01)

(52) U.S. Cl.
USPC ..... Plt./298

(58) Field of Classification Search
USPC ..... Plt./298
CPC ..... A01H 5/0225
See application file for complete search history.

(56) References Cited

PUBLICATIONS

GTITM UPOVROM Plant Variety Database Citation for 'CIDZ0063' as per CA PBR 13-8102; Aug. 20, 2013; 1 page.*

* cited by examiner

*Primary Examiner* — Kent L Bell
(74) *Attorney, Agent, or Firm* — Joshua L. Price

(57) ABSTRACT

A new *Chrysanthemum* plant named 'CIDZ0063'and particularly distinguished by the deep red, daisy-type inflorescences, a very strong, non-fading flower color, compact growth habit, and a flowering response time of 7.5 weeks.

1 Drawing Sheet

Latin name of the genus and species of the plant claimed: *Chrysanthemum×morifolium.*

Varietal denomination: 'CIDZ0063'.

BACKGROUND OF THE NEW PLANT

The present invention comprises a new *Chrysanthemum*, botanically known as *Chrysanthemum×morifolium*, and hereinafter referred to by the variety name 'CIDZ0063'.

'CIDZ0063' is a product of a planned breeding program. The new cultivar has deep red, daisy-type inflorescences, a very strong, non-fading inflorescence color, compact growth habit, and a flowering response time of 7.5 weeks.

'CIDZ0063' originated from a hybridization made in March 2008 in a greenhouse in Bogota, Colombia. The female parent was the unpatented, proprietary plant designated 'D0082', with red, daisy-type inflorescences, having a less vigorous growth, smaller inflorescences and slower flowering response than 'CIDZ0063'.

The male parent of 'CIDZ0063' was the unpatented, proprietary plant designated as 'B0371', with dark pink, daisy-type inflorescences, larger inflorescence size, and a faster flowering response when compared to 'CIDZ0063'.

The resultant seed was sown in July 2009, and the off-spring was grown in Fort Myers, Fla. 'CIDZ0063' was selected as one flowering plant within the progeny of the stated cross in November 2009.

The first act of asexual reproduction of 'CIDZ0063' was accomplished when vegetative cuttings were propagated from the initial selection in March 2010 in a greenhouse in Gilroy, Calif.

BRIEF SUMMARY OF INVENTION

Horticultural examination of plants grown from cuttings of the plant initiated in August 2010, and continuing thereafter, has demonstrated that the combination of characteristics as herein disclosed for 'CIDZ0063' are firmly fixed and are retained through successive generations of asexual reproduction.

'CIDZ0063' has not been observed under all possible environmental conditions. The phenotype may vary significantly with variations in environment such as temperature, light intensity, and day length.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical inflorescence and foliage characteristics of 'CIDZ0063' with colors being as true as possible with an illustration of this type.

Figure 1:
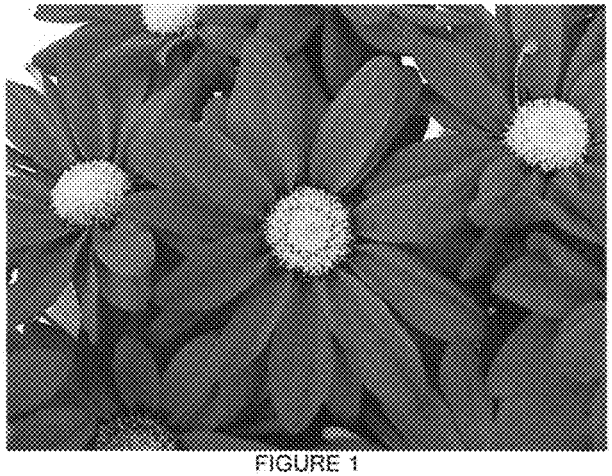
Figure 2:
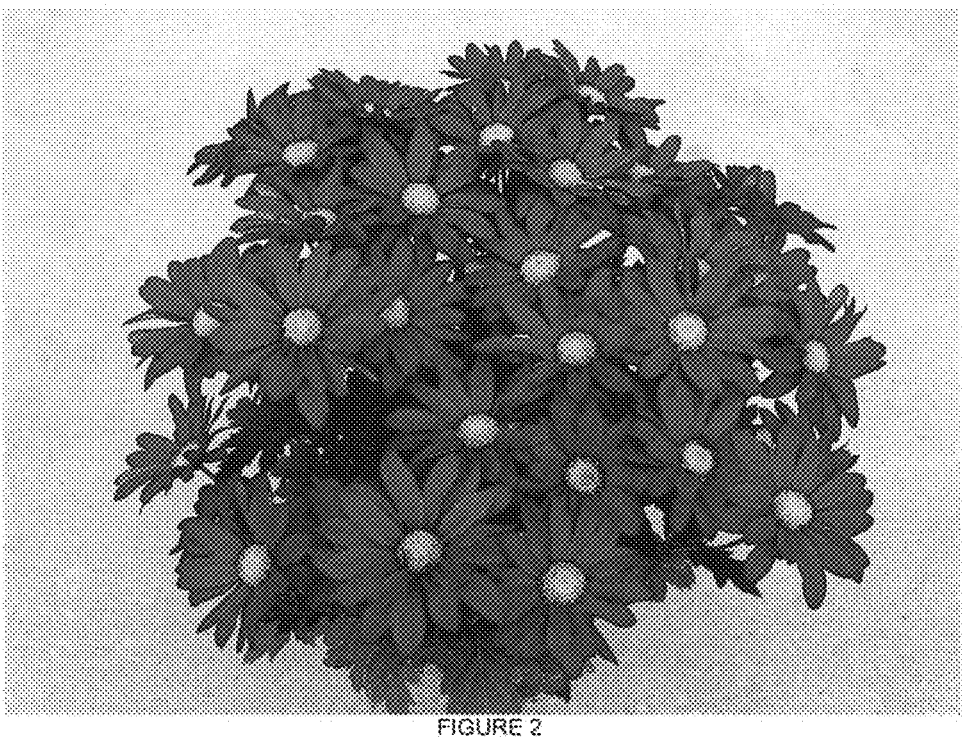

The photographic drawings show in FIG. 1 a close-up of an inflorescence of the new plant and in FIG. 2 a flowering plant.

DETAILED BOTANICAL DESCRIPTION

The plant descriptions and measurements were taken indoors in Nipomo, Calif. on Aug. 14, 2014 on about 11 week old plants. Unrooted cuttings had been planted, 4 plants per pot, in 6 inch pots on May 24, 2014. The plants were pinched and moved to short days on Jun. 16, 2014 to induce flowering.

The aforementioned photographs: FIGS. 1 and 2 were taken in Nipomo, Calif. in May 2013, and showing a plant from a trial, in which flowering had been induced by applying black cloth. These plants were about 10.5 weeks of age. Unrooted cuttings had been planted into in a 6 inch pot in February 2013.

Color references are made to The Royal Horticultural Society Colour Chart (R.H.S.) 2001.

TABLE 1

DIFFERENCES BETWEEN THE NEW VARIETY 'CIDZ0063' AND A MOST SIMILAR VARIETY:

| | 'CIDZ0063' | 'RED YOAUBURN', U.S. Pat. No. PP15,007 |
|---|---|---|
| Flower color: | Deeper red hue | Lighter red hue |
| Flowering response: | Faster | Slower |
| Plant habit: | Shorter and more compact | Taller, more vigorous growth |

Plant:

*Form, growth and habit.*13 Herbaceous pot-type, stems upright, freely branching, strong and moderately vigorous growth habit.

*Plant height.*—20.0-23.0 cm.

*Plant height* (*inflorescence included*).—27.0-30.0 cm.

*Plant width.*—21.0-26.0 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 137A.

*Lower surface.*—Between RHS 138A and RHS 138B.

*Mature, leaf color, upper surface.*—Closest to RHS 137A with some slightly darker mottling.

*Lower surface.*—Between RHS 138A and RHS 138B.

*Length.*—6.0-7.3 cm.

*Width.*—5.2-6.0 cm.

*Shape.*—Ovate.

*Base shape.*—Attenuate.

*Apex shape.*—Mucronulate.

*Margin.*—Palmately lobed; irregularly incised, somewhat serrate.

*Texture, upper surface.*—Bifid T-shaped hairs.

*Lower surface.*—Bifid T-shaped hairs.

*Color of veins, upper surface.*—RHS 144C becoming indistinct.

*Color of veins, lower surface.*—RHS 144C.

*Pattern of veining.*—Palmate.

*Petiole color.*—RHS 144C.

*Length.*—0.8-1.3 cm.

*Diameter.*—0.2-0.25 cm.

*Texture.*—Bifid T-shaped hairs.

Stem:

*Quantity of main branches per plant.*—3-5.

*Color of stem.*—RHS 146A.

*Length of stem.*—About 20.0 cm.

*Diameter.*—0.3-0.5 cm.

*Length of internodes.*—0.7-1.2 cm.

*Texture.*—Bifid T-shaped hairs.

*Color of peduncle.*—RHS 146A.

*Length of peduncle.*—4.0-6.5 cm.

*Peduncle diameter.*—0.2 cm.

*Texture.*—Bifid T-shaped hairs.

Inflorescence:

*Type.*—Compositae type, solitary inflorescences borne terminally above foliage, ray florets arranged acropetally on a capitulum.

*Quantity of short days to flowering* (*response time*).—7.5 weeks.

*Natural season flowering.*—Not determined on this variety.

*Quantity of inflorescences per plant.*—18-34.

*Lastingness of individual blooms on the plant.*—4 weeks.

*Fragrance.*—Slightly spicy.

Bud (just when opening/showing color):

*Color.*—Closest to RHS 53A.

*Length.*—1.5-1.8 cm.

*Width.*—1.7-2.0 cm.

*Shape.*—Oblate.

Immature inflorescence:

*Diameter.*—4.0-5.0 cm.

*Color of ray florets, upper surface.*—Closest to RHS 46A.

*Lower surface.*—Closest to RHS 53A.

Mature inflorescence:

*Diameter.*—8.0-9.5 cm.

*Depth.*—1.5-2.5 cm.

*Total diameter of disc.*—1.8-2.0 cm.

*Receptacle color.*—RHS 144B.

*Receptacle height.*—0.4 cm.

*Receptacle diameter.*—0.6-0.7 cm.

Ray florets:

*Average quantity of florets.*—20-25 in 1 whorl.

*Color of florets, upper surface.*—Closest to RHS 46B.

*Lower surface.*—Closest to 46C.

*Length.*—3.2-3.7 cm.

*Width.*—0.6-0.8 cm.

*Shape.*—Flat.

*Apex shape.*—Praemorse.

*Margin.*—Entire.

*Texture, upper surface.*—Papillose.

*Lower surface.*—Papillose.

Disc florets:

*Average quantity of florets.*—Approximately 200.

*Color of florets.*—RHS 7B basally fading to more RHS 155D with a RHS 7B apex.

*Length.*—1.0-1.6 cm.

*Width.*—0.15-0.3 cm when open.

*Shape.*—Tubular, elongated.

*Apex shape.*—Acute, 5 pointed.

Phyllaries:

*Quantity.*—About 20.

*Color, upper surface.*—Lighter than RHS 138B.

*Lower surface.*—RHS 138B.

*Length.*—0.5-0.7 cm.

*Width.*—0.15-0.2 cm.

*Shape*.—Lanceolate.
*Apex shape*.—Acute.
*Base*.—Fused.
*Margins*.—Entire; slightly papery.
*Texture, upper surface*.—Glabrous.
*Lower surface*.—Bifid T-shaped hairs.

Reproductive organs:

*Pistil*.—1, found on both types of florets.
*Length*.—0.6 cm.
*Style color*.—RHS 155C.
*Style length*.—0.45 cm.
*Stigma color*.—RHS 17C.
*Stigma shape*.—Bi-parted.
*Ovary color*.—RHS 155C but more translucent.
*Stamens*.—4, found only on the disc florets.
*Color of filaments*.—RHS 155C.
*Length filaments*.—0.4-0.5 cm.
*Anther color*.—RHS 15A.
*Anther length*.—0.15 cm.
*Anther shape*.—Oval.
*Color of pollen*.—RHS 17B.
*Pollen amount*.—Abundant.
*Fertility/seed set*.—Has not been observed to date.
*Disease/pest resistance*.—Has not been observed to date.

What is claimed is:

1. A new and distinct variety of *Chrysanthemum* plant named 'CIDZ0063' substantially as illustrated and described herein.

* * * * *